United States Patent
Nisbet et al.

(10) Patent No.: US 7,732,630 B2
(45) Date of Patent: Jun. 8, 2010

(54) PROCESS FOR THE PREPARATION OF AN ALKANEDIOL AND A DIALKYL CARBONATE

(75) Inventors: Timothy Michael Nisbet, Amsterdam (NL); Garo Garbis Vaporciyan, Houston, TX (US); Cornelis Leonardus Maria Vrouwenvelder, Amsterdam (NL); Paul Wood, Amsterdam (NL)

(73) Assignee: Shell Oil Company, Houston, TX (US)

( * ) Notice: Subject to any disclaimer, the term of this patent is extended or adjusted under 35 U.S.C. 154(b) by 226 days.

(21) Appl. No.: 12/017,296

(22) Filed: Jan. 21, 2008

(65) Prior Publication Data

US 2008/0200711 A1 Aug. 21, 2008

(30) Foreign Application Priority Data

Jan. 23, 2007 (EP) .................. 07100971

(51) Int. Cl.
*C07C 69/96* (2006.01)
(52) U.S. Cl. ...................................... 558/277
(58) Field of Classification Search ................ 558/277; 568/858
See application file for complete search history.

(56) References Cited

U.S. PATENT DOCUMENTS

| | | | |
|---|---|---|---|
| 2,448,767 A | 9/1948 | Carlson | 260/284 |
| 3,803,201 A | 4/1974 | Gilpin | 260/463 |
| 4,062,884 A | 12/1977 | Romano et al. | 260/463 |
| 4,691,041 A | 9/1987 | Duranleau et al. | 558/277 |
| 5,210,268 A | 5/1993 | Fukuoka et al. | 558/270 |
| 5,344,954 A | 9/1994 | Schon et al. | 558/274 |
| 5,359,118 A | 10/1994 | Wagner et al. | 558/277 |
| 5,747,609 A | 5/1998 | Komiya et al. | 526/68 |
| 6,156,160 A | 12/2000 | Marquis et al. | 203/29 |
| 6,207,850 B1 * | 3/2001 | Jiang et al. | 558/277 |
| 6,620,959 B1 | 9/2003 | Buchanan et al. | 558/277 |
| 6,768,020 B2 | 7/2004 | De Jonge et al. | 558/277 |
| 6,835,858 B1 | 12/2004 | De Jonge et al. | 568/716 |
| 6,930,195 B2 | 8/2005 | Buchanan et al. | 558/277 |
| 6,953,864 B2 | 10/2005 | De Jonge et al. | 558/277 |
| 7,563,919 B2 * | 7/2009 | Van Der Heide et al. | 558/277 |

FOREIGN PATENT DOCUMENTS

| | | |
|---|---|---|
| EP | 1082 | 3/1979 |
| EP | 274953 | 7/1988 |
| EP | 180387 | 5/1990 |
| EP | 569812 | 11/1993 |
| EP | 889025 | 1/1999 |
| EP | 1245608 | 5/2004 |
| EP | 1065193 | 7/2004 |
| EP | 0850972 | 6/2006 |
| JP | 0940616 | 2/1997 |
| WO | WO03/006418 | 1/2003 |
| WO | WO2005/003113 | 1/2005 |

OTHER PUBLICATIONS

Ullmann's Encyclopedia of Industrial Chemistry, 5$^{th}$ ed. vol. B4, pp. 321 ff, 1992.
J F Knifton et al., J. Mol. Catal, 67 (1991) 389ff.
Hong Zhu, Li-Ban Chen and Ying-Yan Jiang, Synthesis of Propylene Carbonate and Some Dialkyl Carbonates in the Presence of Bifunctional Catalyst Compositions, Polymers for Advanced Technologies, Wiley & Sons, Bognor Regis, GB, vol. 7, No. 8, Aug. 1, 1996, pp. 701-703, XP000623427.

* cited by examiner

*Primary Examiner*—Rei-tsang Shiao

(57) ABSTRACT

An alkanediol and a dialkyl carbonate are prepared in a process comprising:
(a) reacting an alkylene carbonate and an alkanol feedstock in a reaction zone under transesterification conditions to obtain a product mixture of dialkyl carbonate, unconverted alkanol, the alkanediol, and unconverted alkylene carbonate;
(b) separating dialkyl carbonate and unconverted alkanol from the product mixture to obtain a bottom product stream containing alkanediol and unconverted alkylene carbonate;
(c) recovering the dialkyl carbonate; and
(d) separating alkanediol from the bottom product stream to leave a recycle stream comprising unconverted alkylene carbonate,
wherein the recycle stream comprising unconverted alkylene carbonate is split in at least two portions, and at least one portion is recycled to the reaction zone and another portion is subjected to hydrolysis to yield alkanediol and carbon dioxide.

16 Claims, 1 Drawing Sheet

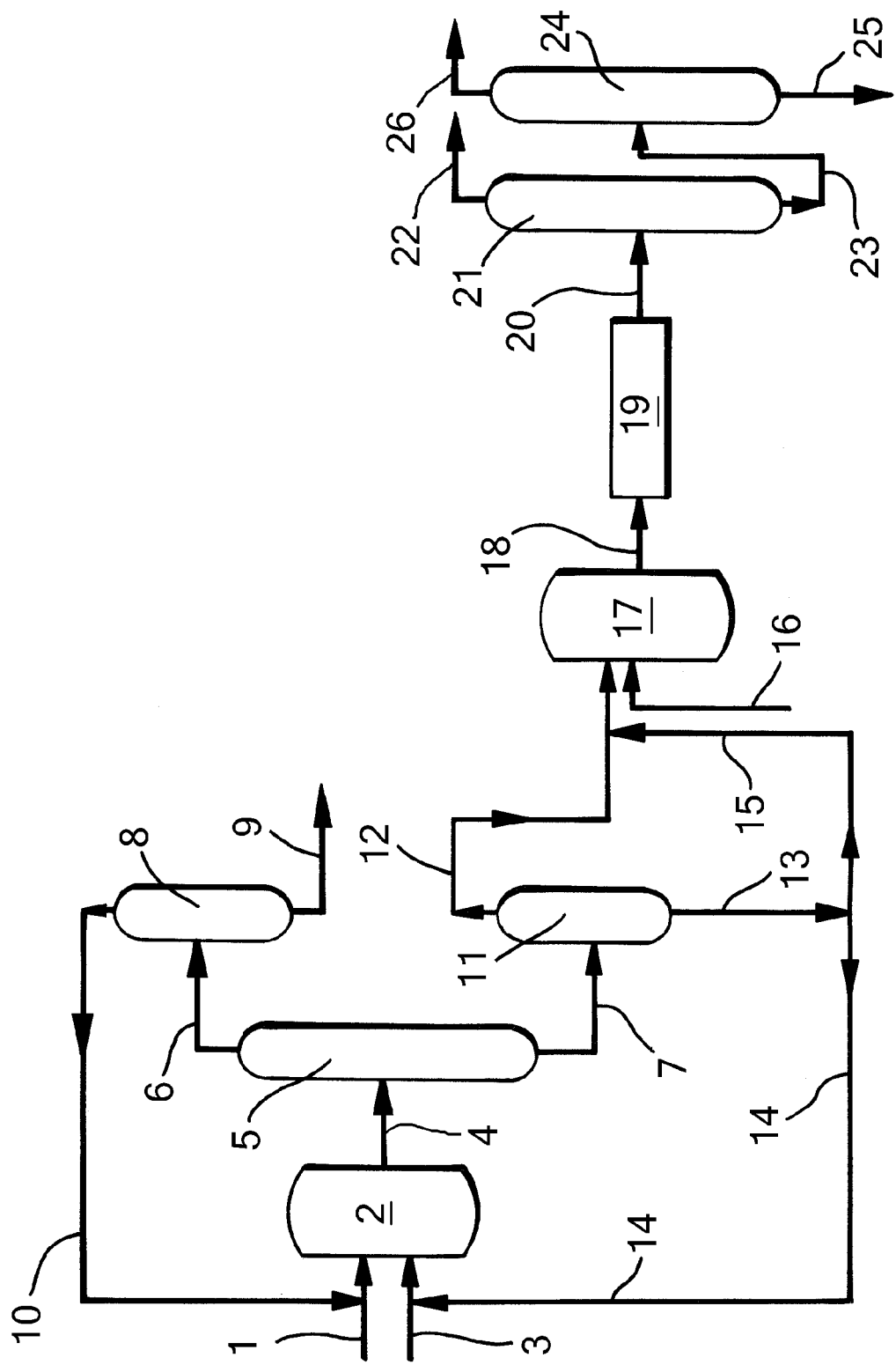

PROCESS FOR THE PREPARATION OF AN ALKANEDIOL AND A DIALKYL CARBONATE

This application claims the benefit of European Patent Application No. 07100971.6 filed on Jan. 23, 2007 that is hereby incorporated by reference.

FIELD OF THE INVENTION

The present invention relates to a process for the preparation of an alkanediol and a dialkyl carbonate. More particularly, the invention relates to a process for the preparation of such compounds from an alkylene carbonate and an alkanol.

BACKGROUND OF THE INVENTION

Such a process is described in e.g. U.S. Pat. No. 5,359,118. The patent discloses a process in which di($C_1$-$C_4$ alkyl) carbonates are prepared by transesterification of an alkylene carbonate with a $C_1$-$C_4$ alkanol. The alkylene carbonate and an alkanol feedstock are reacted countercurrently in a column with the aid of a catalyst. The catalyst is usually homogeneous, although the use of heterogeneous catalysts is also suggested. The alkylene carbonate is introduced into the upper part of the column and trickles down from above. The alkanol feedstock comprising a pure alkanol and a stream, comprising the alkanol and also the dialkyl carbonate, is fed into the column at a lower part. The alkanol flows upward and reacts countercurrently with the alkylene carbonate to obtain dialkyl carbonate with unreacted alkanol as the top effluent and the alkanediol with any entrained alkanol as the bottom effluent. The top effluent is subjected to distillation to yield an alkanol-rich stream comprising the alkanol and minor amounts of the dialkyl carbonate. This stream is fed to the column as part of the alkanol feedstock. The bottom stream is worked-up resulting in an alkylene glycol stream and a catalyst-containing concentrate.

The patent discloses the formation of high-boiling by-products, such as polyglycols. In the known process these high-boiling by-products are contained in the catalyst-containing concentrate. Part of the concentrate is recycled to the transesterification, whereas another part is discarded.

Although the process discloses the formation of polyglycols, it does not address the problem of the removal of such polyglycols, in particular the diglycols. Further, the patent does not acknowledge that polyglycols may be present in the alkylene carbonate feed material. Moreover, the patent presumes that no alkylene carbonate leaves the reactor unconverted. In practice, the transesterification to dialkyl carbonate will not be 100%. Therefore, the bottom product of the process will contain not only polyglycols, as suggested in U.S. Pat. No. 5,359,118, but also some unconverted alkylene carbonate. In view of their boiling points it is very difficult to separate polyglycols, in particular, dialkylene glycols from the corresponding alkylene carbonates. This has not been acknowledged in the process according to U.S. Pat. No. 5,359,118.

It has now been found that the build up of higher-boiling by-products can be prevented by subjecting a part of a stream containing alkylene carbonate and polyglycols to a hydrolysis step, thereby obtaining alkylene glycol, which is a valuable compound.

SUMMARY OF THE INVENTION

The present invention provides a process for the preparation of an alkanediol and a dialkyl carbonate comprising:
(a) reacting an alkylene carbonate and an alkanol feedstock into a reaction zone under transesterification conditions to obtain a product mixture of dialkyl carbonate, unconverted alkanol, the alkanediol, and unconverted alkylene carbonate;
(b) separating dialkyl carbonate and alkanol from the product mixture to obtain a bottom product stream containing alkanediol and unconverted alkylene carbonate;
(c) recovering the dialkyl carbonate; and
(d) separating alkanediol from the bottom product stream to leave a recycle stream comprising unconverted alkylene carbonate, wherein the recycle stream comprising unconverted alkylene carbonate is split in at least two portions, and at least one portion is recycled to the reaction zone and another portion is subjected to hydrolysis to yield alkanediol and carbon dioxide.

The present process entails the advantages that part of the alkylene carbonate in the recycle stream is subjected to the transesterification again, such that it may be converted to the target dialkyl carbonate. Further, the alkylene carbonate in the portion that is subjected to hydrolysis is not completely lost, since it is converted into carbon dioxide and alkanediol so that at least one of the target products is being obtained. Furthermore, the process prevents a build-up of polyglycols that may be present in the recycle stream, in the reaction system. Moreover, any polyglycols that are present in the portion of the recycle stream that is being subjected to hydrolysis will be contained in a stream that comprises polyglycols and alkanediol and not alkylene carbonate. Therefore, it is relatively easy to separate the polyglycols from this mixture, in contrast to the separation of polyglycols from a mixture that also comprises alkylene carbonate. In the latter mixtures, separation is very cumbersome.

BRIEF DESCRIPTION OF THE DRAWINGS

FIG. 1 depicts a flow scheme for the process according to the present invention.

DETAILED DESCRIPTION OF THE INVENTION

The present invention provides a process for the preparation of an alkanediol and a dialkyl carbonate. The reaction zone in the present invention may be a reactive distillation zone, as described in U.S. Pat. No. 5,359,118. This would entail that the reaction is carried out counter-currently. The transesterification reaction is advantageously conducted in a column furnished with internals, like a distillation column. Hence, it may contain trays with bubble caps, sieve trays, or Raschig rings. The skilled person will realise that several packing types and tray configurations will be possible. Suitable columns have been described in, e.g., Ullmann's Encyclopedia of Industrial Chemistry, $5^{th}$ ed. Vol. B4, pp 321 ff, 1992. The alkylene carbonate will be fed at the upper part of such a column and will flow down. The alkylene carbonate will generally have a higher boiling point than the alkanol. In the case of ethylene and propylene carbonate the atmospheric boiling points are above 240° C. The alkylene carbonate will flow down over the trays or rings and be brought into contact with the alkanol that flows upward.

In a preferred embodiment the reaction is conducted in a co-current manner. A suitable way to operate is to carry out the reaction in a trickle-flow manner wherein the reactants, part in vapor phase and part in liquid phase, drip down over a heterogeneous catalyst. A more preferred way to operate the process of the present invention is in a liquid full reactor. A suitable reaction zone of this type is a pipe-type reaction zone wherein the reaction is conducted in a plug flow manner. This will enable the reaction to run to virtual completion. A further possibility is to conduct the reaction in a continuously stirred tank reactor (CSTR). In the latter case the effluent from the CSTR is preferably subjected to a post-reaction in a plug flow reactor so that the reaction runs to virtual completion.

The process of the present invention includes the transesterification of an alkylene carbonate with an alkanol. This transesterification reaction is described in U.S. Pat. No. 5,359,118. The starting materials of the transesterification are preferably selected from $C_2$-$C_6$ alkylene carbonate and $C_1$-$C_4$ alkanols. More preferably the starting materials are ethylene carbonate or propylene carbonate and methanol, ethanol or isopropanol.

Transesterification conditions suitably include the presence of a catalyst. Suitable homogeneous catalysts have been described in U.S. Pat. No. 5,359,118 and include hydrides, oxides, hydroxides, alcoholates, amides, or salts of alkali metals, i.e., lithium, sodium, potassium, rubidium and cesium. Preferred catalysts are hydroxides or alcoholates of potassium or sodium. It is advantageous to use the alcoholate of the alkanol that is being used as feedstock. Such alcoholate can be added as such or be formed in situ.

Other suitable catalysts are alkali metal salts, such as acetates, propionates, butyrates, or carbonates. Further suitable catalysts are described in U.S. Pat. No. 5,359,118 and the references mentioned therein, such as EP 274 953, U.S. Pat. No. 3,803,201, EP 1082, and EP 180 387.

As indicated in U.S. Pat. No. 5,359,118, it is also possible to employ heterogeneous catalysts. In the current process the use of heterogeneous catalysts in the transesterification reaction is preferred. Suitable heterogeneous catalysts include ion exchange resins that contain functional groups. Suitable functional groups include tertiary amine groups and quaternary ammonium groups, and also sulfonic acid and carboxylic acid groups. Further suitable catalysts include alkali and alkaline earth silicates. Suitable catalysts have been disclosed in U.S. Pat. Nos. 4,062,884 and 4,691,041. Preferably, the heterogeneous catalyst is selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff.

The transesterification conditions are known to one of ordinary skill in the art and suitably include a temperature from 40 to 200° C., and a pressure from 50 to 5000 kPa (0.5 to 50 bar). When the alkanol is methanol, the pressure is preferably close to atmospheric. The temperature depends on the alkanol feedstock and pressure used, and the reactor used. In countercurrent mode the temperature is kept such that it is close to and above the boiling point of the alkanol, e.g. up to 5° C. above the boiling point. In the case of methanol and atmospheric pressure, the temperature is close to and above 65° C., for instance between 65 and 70° C. In case of co-current operation the alkanol may still be liquid. In co-current operation, the pressure ranges suitably from 0.5 to 50 bar, preferably from 2 to 20 bar, and the temperature from 40 to 200° C., preferably from 80 to 160° C.

When the transesterification catalyst is homogeneous such as an alkali metal alcoholate, and when a reactive distillation is being employed, the homogeneous catalyst, may be introduced in the upper part of the reaction zone. The alkanol feedstock is then introduced at a lower point. The feedstock may be completely in vapor phase. However, it is also possible to introduce the feedstock into the column partly in the liquid phase. It is believed that the liquid phase ensures a higher concentration of alkanol in the lower part of the column with a beneficial effect on the overall transesterification. It is distributed over the width of the column via the inlet and the column internals. The ratio between the vapor and the liquid part of the alkanol feedstock may be varied between wide ranges. The vapor/liquid weight ratio is suitably from 1:1 to 10:1 wt/wt.

When a heterogeneous catalyst bed is being used and when a reactive distillation is being employed, the alkylene carbonate is suitably introduced above the catalyst bed and the alkanol below the catalyst bed. When a co-currently operated reactor is being employed the reactants may be pre-mixed or introduced separately into the reactor upstream of the catalyst bed. The person skilled in the art will know that the transesterification is an equilibrium reaction. Therefore, he may suitably employ an excess of the alkanol. The molar ratio of alkanol to alkylene carbonate is suitably from 1.01:1 to 25:1, preferably from 2:1 to 15:1, more preferably from 3:1 to 7:1. The amount of catalyst can evidently be much smaller. In case of the use of a homogeneous catalyst suitable amounts of such catalysts include from 0.1 to 5.0% wt based on alkylene carbonate, preferably from 0.2 to 2% wt. The weight hourly space velocity may suitably range from 0.1 to 100 kg/kg.hr.

From the reaction zone a mixture of dialkyl carbonate, unconverted alkanol, alkanediol and unconverted alkylene carbonate is withdrawn. In the case of a counter-current process, such as reactive distillation, a first mixture of alkanol and dialkyl carbonate is withdrawn at the top of the reactive distillation column, and at the bottom a second mixture comprising unconverted alkylene carbonate and alkanediol. In case of a co-current operation a product mixture comprising the above-mentioned four compounds is obtained.

When the transesterification is being conducted in a reactive distillation zone unconverted alkanol and dialkyl carbonate together are separated together in the reactive distillation zone via the upper part of the reactive distillation column. Alkanediol and unconverted alkylene carbonate are withdrawn from the reactive distillation column at the lower part. In other embodiments the four compounds are withdrawn simultaneously. In one embodiment the unconverted alkanol and the dialkyl carbonate are separated by distillation in one single fraction. Suitable distillation conditions are a pressure from 0.1 to 1.0 bar and a temperature from 40 to 300° C. This achieves the separation of a top fraction comprising unconverted alkanol and dialkyl carbonate and a bottom fraction comprising unconverted alkylene carbonate and alkanediol. The top fraction is preferably subjected to another distillation to separate dialkyl carbonate from unconverted alkanol. Such distillation may suitably be achieved at pressures ranging from subatmospheric pressure to superatmospheric pressure. Suitably the pressure may vary from 0.1 to 45 bar. Temperatures may vary in accordance with the pressure selected. The temperature may be from 35 to 300° C. More preferably, the conditions in the distillation include a pressure ranging from 0.1 to 0.5 bar and a temperature ranging from 35 to 150° C.

When the dialkyl carbonate and the alkanol form an azeotrope it may be beneficial to use extractive distillation, using an extractant to facilitate the separation between the dialkyl carbonate and the alkanol. The extractant can be selected from many compounds, in particular alcohols such as phenol, or anisole. However, it is preferred to employ an alkylene carbonate as extractant. It is most advantageous to obtain the separation in the presence of the alkylene carbonate that is being used as starting material for the eventual alkanediol.

In another embodiment the product stream is subjected to distillation in such a manner that mainly unconverted alkanol is separated as top fraction. Such a distillation may suitably be carried out at a pressure of 0.1 to 45 bar. Temperatures may vary in accordance with the pressure selected. The temperature may be from 35 to 300° C. and preferably, the pressure is from 0.5 to 1.5 bar and the temperature ranges from 60 to 200° C. In a further distillation the remaining compounds may be separated in dialkyl carbonate as top fraction and a bottom fraction comprising alkanediol and unconverted alkylene carbonate. Conditions for this distillation advantageously include a pressure of 0.1 to 0.5 bar and a temperature of 60 to 190° C.

The dialkyl carbonate recovered in the embodiments may optionally be further purified. This further purification may comprise a further distillation step or an ion-exchange step, as described in U.S. Pat. No. 5,455,368.

Both in the counter-current and the co-current embodiments a bottom product is obtained comprising alkanediol and unconverted alkylene carbonate. To separate alkanediol from this bottom stream the bottom stream is preferably subjected to a further distillation step, suitably at a pressure from 0.01 to 0.4 bar and a temperature of 100 to 200° C. This distillation achieves a separation of alkanediol and a recycle stream comprising unconverted alkylene carbonate. The recovered alkanediol recovered as the top fraction in this distillation may comprise other compounds, such as unconverted alkylene carbonate depending on the sharpness of the separation cut.

The recycle stream is split in at least two portions, two being usually sufficient. At least one portion is recycled to the reaction zone thereby enabling further reaction of any unconverted alkylene carbonate. Another portion is subjected to a hydrolysis thereby preventing the build-up of heavy by-products such as polyglycols in the process, and at the same time forming alkanediol that can be recovered as product. Optionally, the stream may be split in three or more portions, the additional portions being bled from the process. It will be understood that in general the bleed stream will be as small as feasible, and preferably, no bleed stream will be used in the process.

The weight ratio between the two portions can be selected by the skilled person to arrive at the optimal effect. It is advantageous to split the recycle stream such that the weight ratio between the portion to be recycled and the portion to be subjected to hydrolysis is from 0.1:1 to 200:1, preferably from 10:1 to 150:1, more preferably from 20:1 to 100:1. This will allow an efficient prevention of build-up of heavy compounds and give satisfactory additional use of unconverted alkylene carbonate.

The hydrolysis of alkylene carbonate with water is described in the art. Reference is made to, e.g., U.S. Pat. No. 5,847,189. Hydrolysis usually takes place in the presence of a catalyst. The catalyst may be a homogeneous catalyst, for instance a mineral acid such as nitric acid, sulfuric acid or hydrochloric acid, basic compounds, such as alkali metal hydroxides or alkaline earth metal hydroxides or carbonates, tertiary amines, such as triethyl amine, tributyl amine, trihexyl amine or benzyl diethyl amine, quaternary phosphonium or ammonium salts, alkali metal alkanolates, and other catalysts as mentioned in U.S. Pat. No. 5,847,189. Alternatively, the catalyst may be heterogeneous. Examples are given in WO 2004/085375, and include alumina, silica-alumina, silica-magnesia, gallium silicate, zeolites, metal-exchanged zeolites, ammonium-exchanged zeolites, zinc oxide or zinc hydroxide on a support, lanthanum oxide on a support, a mixture of aluminium and magnesium oxides or hydroxides and ion-exchange resins. Preferably, the catalyst is selected from the group consisting of a mixture of aluminium and magnesium oxides as disclosed in U.S. Pat. No. 6,953,864, supported zinc catalyst as described in U.S. Pat. No. 6,835,858, and lanthanum supported on a carrier, as elaborated in U.S. Pat. No. 6,768,020. More preferably, the catalyst is selected from the group consisting of alkali metal and alkaline earth metal hydroxides and carbonates. Sodium and potassium carbonates are most preferred.

The hydrolysis is preferably carried out at a temperature ranging from 50 to 300° C., more preferably from 100 to 200° C. The pressure may vary widely. Suitably the pressure is from 0.5 to 100 bar, more preferably from 1 to 50, most preferably from 1 to 30 bar.

In an alternative embodiment the hydrolysis is carried out in a reactive distillation. In this embodiment water is fed into the lower part of a hydrolysis unit. The portion of the recycle stream comprising unconverted alkylene carbonate is passed to the hydrolysis unit via an inlet at the upper part thereof. If a homogeneous catalyst is being used it is also fed into the upper part of the hydrolysis unit, preferably together with the alkylene carbonate-containing stream. Contact between reactants then takes place on trays, Raschig rings and/or other packing types that have been provided in the hydrolysis unit. When the hydrolysis unit contains a bed of heterogeneous catalyst the contact between water and alkylene carbonate takes place on this bed. Water is vaporised and water vapor flows upward in the hydrolysis unit. Alkylene carbonate flows downward in the liquid form and is contacted either at the packing in the hydrolysis unit or via the bed of catalyst with water vapor. The reaction results in alkanediol and carbon dioxide. Carbon dioxide and any water vapor that is unreacted is withdrawn from the unit at the top of the hydrolysis unit. Alkanediol and any other higher-boiling material, including polyglycols, unconverted alkylene carbonate, if any, and catalyst, if present, is discharged at the bottom part of the unit.

The conditions in this preferred embodiment are a temperature ranging from 120 to 300° C. and a pressure from 0.1 to 25 bar.

Depending on the effectiveness of the separation of the bottom stream comprising alkanediol and unconverted alkylene carbonate, the alkanediol product stream may comprise minor amounts of alkylene carbonate. Such amounts may range from 0 to 10% wt, based on the total weight of alkanediol and alkylene carbonate. It is advantageous to subject this stream to hydrolysis thereby converting unconverted alkylene carbonate into alkanediol, thereby increasing the yield on alkanediol. More preferably the alkanediol recovered from the bottom stream and a portion of the recycle stream are subjected to the same hydrolysis in the same hydrolysis unit.

Carbon dioxide that is produced in the hydrolysis unit may be discharged. However, from an economic and also from an environmental standpoint such discharge is undesired. Preferably the carbon dioxide is re-used. Since alkylene carbonate is prepared from alkylene oxide and carbon dioxide it is preferred to use carbon dioxide in the preparation of alkylene carbonate, more preferably in the preparation of alkylene carbonate that is being used in the process of the present invention. The preparation of alkylene carbonate from carbon dioxide and alkylene oxide is known. The preparation is carried out in the presence of a catalyst. Suitable catalysts include tetraalkyl phosphonium halides, as disclosed in, e.g., WO 2005/003113. An excellent example is tetrabutyl phosphonium bromide. The use of ammonium halides as catalysts in such preparation has been disclosed in U.S. Pat. No. 6,156,160. Examples include tetramethyl ammonium bromide, tetraethyl ammonium bromide and benzyl triethyl ammonium bromide.

The alkanediol that is recovered from the hydrolysis is advantageously fractionated to obtain a purified alkanediol stream and a bottom stream comprising polyglycols, catalyst, if present, and other higher boiling contaminants. When the alkanediol that is separated from the unconverted alkylene carbonate-comprising bottom stream is combined with the relevant portion of the recycle stream and passed to the hydrolysis a purified alkanediol stream results as product.

The process of the present invention can be employed for a variety of feedstocks. The process is excellently suited for the preparation of ethylene glycol (1,2-ethanediol), propylene glycol (1,2-propanediol), dimethyl carbonate and/or diethyl carbonate and/or diisopropyl carbonate. The process is most advantageously used for the production of ethylene glycol or propylene glycol and diethyl carbonate or diisopropyl carbonate from ethylene carbonate or propylene carbonate and ethanol or isopropanol.

In FIG. 1, a flow scheme for the process according to the present invention is shown. Although the process will be described for ethanol as a suitable alcohol and ethylene carbonate as the alkylene carbonate the skilled person will understand that other alkanols and alkylene carbonates can be similarly used.

Ethanol is passed via line 1 into a reactor 2. Reactor 2 can suitably be a plug flow reactor. Via line 3 ethylene carbonate is also fed into the reactor 2. A transesterification catalyst may be present or may be fed continuously in the reactor. The catalyst may be mixed with one of the reactants or fed to the reactor via a separate line (not shown). A product comprising a mixture of diethyl carbonate, unconverted ethanol, ethylene glycol and unconverted ethylene carbonate is withdrawn from the reactor 2 via line 4. Via line 4 the mixture is passed to a distillation column 5 where the product is separated into a top fraction comprising diethyl carbonate and ethanol that is withdrawn via line 6, and a bottom fraction comprising ethylene glycol and ethylene carbonate withdrawn via line 7. The mixture comprising diethyl carbonate and ethanol in line 6 is passed to a distillation column 8, where the mixture is separated into ethanol and diethyl carbonate. The diethyl carbonate is discharged via line 9 and recovered as product, optionally after further purification. Ethanol is recovered via line 10 and recycled to the reactor 2 via line 1.

The bottom stream in line 7 is subjected to distillation in a distillation column 11. In the distillation column 11 a top product comprising ethylene glycol contaminated with some ethylene carbonate is recovered via line 12. The bottom product of distillation column 11 withdrawn via line 13 comprises polyethylene glycol, in particular diethylene glycol, and ethylene carbonate. The stream of line 13 is split. One portion is recycled to the reactor 2 via line 14 and line 3. A second portion is withdrawn via line 15 and combined with the top product of distillation column 11 comprising ethylene glycol contaminated with some ethylene carbonate in line 12. Via line 16 water is fed into a hydrolysis reactor 17, into which also the combined fractions from line 12 and 15 are introduced into a hydrolysis reactor 17. Reactor 17 is shown as a continuously stirred tank reactor (CSTR), but the skilled person may also employ a reactive distillation column. In case of a CSTR the product is preferably withdrawn via line 18 and passed to a plug flow pipe reactor, indicated in the figure as reasctor 19 to allow the reaction to go to completion. Via line 20 the eventual product of the hydrolysis in reactors 17 and 19 is sent to distillation column 21. Via line 22 water and carbon dioxide are withdrawn as top fraction. The bottom fraction, comprising ethylene glycol and polyglycols are passed via line 23 to a further distillation column 24. The bottom product, comprising the heavy polyglycols is discharged via line 25. The top product comprising ethylene glycol is withdrawn and recovered via line 26.

What is claimed is:

1. A process for the preparation of an alkanediol and a dialkyl carbonate comprising:
    (a) reacting an alkylene carbonate and an alkanol feedstock in a reaction zone under transesterification conditions to obtain a product mixture of dialkyl carbonate, unconverted alkanol, alkanediol and unconverted alkylene carbonate;
    (b) separating dialkyl carbonate and unconverted alkanol from the product mixture to obtain a bottom product stream containing alkanediol and unconverted alkylene carbonate;
    (c) recovering the dialkyl carbonate; and
    (d) separating alkanediol from the bottom product stream to leave a recycle stream comprising unconverted alkylene carbonate,
    wherein the recycle stream comprising unconverted alkylene carbonate is split in at least two portions, and at least one portion is recycled to the reaction zone and another portion is subjected to hydrolysis to yield alkanediol and carbon dioxide.

2. A process as claimed in claim 1, wherein the reaction is conducted in a co-current manner.

3. A process as claimed in claim 2, wherein the reaction is conducted in a plug flow manner.

4. A process as claimed in claim 1, wherein heterogeneous catalysts are used in the transesterification reaction.

5. A process as claimed in claim 1, wherein the temperature in the reaction zone is from 40 to 200° C., and the pressure is from 0.5 to 50 bar.

6. A process as claimed in claim 1, wherein the unconverted alkanol and the dialkyl carbonate are separated by distillation in one fraction.

7. A process as claimed in claim 1, wherein the bottom stream is subjected to a further distillation to achieve a separation of alkanediol and a recycle stream comprising unconverted alkylene carbonate.

8. A process as claimed in claim 7, wherein the alkanediol separated contains unconverted alkylene carbonate.

9. A process as claimed in claim 1, wherein the recycle stream is split such that the weight ratios between the portion to be recycled and the portion to be subjected to hydrolysis range from 0.1:1 to 200:1.

10. A process as claimed in claim 1, wherein the hydrolysis is carried out at a temperature ranging from 50 to 300° C., more preferably from 100 to 200° C. and at a pressure being from 0.5 to 100 bar, more preferably from 1 to 50, most preferably from 1 to 30 bar.

11. A process as claimed in claim 1, wherein the hydrolysis is carried out at a temperature ranging from 100 to 200° C. and at a pressure being from 1 to 50 bar.

12. A process as claimed in claim 1, wherein the hydrolysis is carried out as a reactive distillation.

13. A process as claimed in claim 1, wherein the alkanediol recovered from the bottom stream and a portion of the recycle stream are subjected to the same hydrolysis.

14. A process as claimed in claim 1, wherein the carbon dioxide produced in the hydrolysis is used in the preparation of alkylene carbonate.

15. A process as claimed in claim 1, wherein the alkylene carbonate is selected from the group consisting of ethylene carbonate and propylene carbonate.

16. A process as claimed in claim 1, wherein the alkanol is selected from the group consisting of ethanol and isopropanol.

\* \* \* \* \*